(12) United States Patent
Roy

(10) Patent No.: US 9,051,544 B2
(45) Date of Patent: Jun. 9, 2015

(54) METHOD OF ENHANCING CELL GROWTH USING ALKYL-AMINE-N-OXIDE (AANOX)

(75) Inventor: Sylvain Roy, Savagnier (CH)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 161 days.

(21) Appl. No.: 12/650,095

(22) Filed: Dec. 30, 2009

(65) Prior Publication Data

US 2010/0233805 A1 Sep. 16, 2010

Related U.S. Application Data

(60) Provisional application No. 61/141,555, filed on Dec. 30, 2008.

(51) Int. Cl.
*C12N 15/85* (2006.01)
*C12N 5/00* (2006.01)

(52) U.S. Cl.
CPC .......... *C12N 5/0031* (2013.01); *C12N 2500/46* (2013.01); *C12N 2500/76* (2013.01)

(58) Field of Classification Search
None
See application file for complete search history.

(56) References Cited

U.S. PATENT DOCUMENTS

| | | | |
|---|---|---|---|
| 4,757,006 | A | 7/1988 | Toole et al. |
| 5,378,612 | A | 1/1995 | Nakashima et al. |
| 5,741,705 | A | 4/1998 | Blom et al. |
| 5,994,129 | A | 11/1999 | Armstrong et al. |
| 6,048,729 | A | 4/2000 | Selden et al. |
| 6,063,630 | A | 5/2000 | Treco et al. |
| 6,103,529 | A | 8/2000 | Price et al. |
| 2008/0227136 | A1 | 9/2008 | Pla et al. |

FOREIGN PATENT DOCUMENTS

| | | |
|---|---|---|
| EP | 0403238 | 12/1990 |
| EP | 0481791 | 4/1992 |
| JP | 08-070859 | 3/1996 |
| JP | 11-243942 | 9/1999 |
| WO | WO-96/15231 | 5/1996 |
| WO | WO-96/26266 | 8/1996 |
| WO | WO-98/08934 | 3/1998 |
| WO | WO-98/15614 | 4/1998 |
| WO | WO-00/03000 | 1/2000 |
| WO | WO-01/23527 | 4/2001 |
| WO | WO-2006/045438 | 5/2006 |
| WO | WO-2008/033517 A2 | 3/2008 |

OTHER PUBLICATIONS

Needleman et al., A general method applicable to the search for similarities in the amino acid sequence of two proteins. *J. Mol. Biol.* 48: 443-53 (1970).
Pearson et al., Improved tools for biological sequence comparison. *Proc. Natl. Acad. Sci. USA*, 85: 2444-8 (1988).
Smith et al., Comparison of biosequences. *Adv. Appl. Math.* 2: 482-9 (1981).
Franek et al., Plant protein hydrolysates: preparation of defined peptide fractions promoting growth and production in animal cells cultures. *Biotechnol. Prog.* 16(5):688-92 (2000).
Genbank Accession No. NP_000119, Coagulation factor XI precursor, Sep. 19, 2010.
Genbank Accession No. NP_000120, Coagulation factor XIII A chain precursor, Oct. 3, 2010.
Genbank Accession No. NP_000121, Coagulation factor V precursor, Sep. 20, 2010.
Genbank Accession No. NP_000122, Coagulation factor VII isoform a precursor, Sep. 20, 2010.
Genbank Accession No. NP_000123, Coagulation factor VIII isoform a precursor, Oct. 10, 2010.
Genbank Accession No. NP_000124, Coagulation factor IX preproprotein, Sep. 19, 2010.
Genbank Accession No. NP_000303, Vitamin K-dependent C preproprotein, Oct. 10, 2010.
Genbank Accession No. NP_000479, Antithrombin-III precursor, Sep. 20, 2010.
Genbank Accession No. NP_000495, Coagulation factor X preproprotein, Oct. 3, 2010.
Genbank Accession No. NP_000496, Coagulation factor XII precursor, Sep. 26, 2010.
Genbank Accession No. NP_000497, Prothrombin preproprotein, Sep. 20, 2010.
Genbank Accession No. NP_000543, von Willebrand factor preproprotein, Oct. 6, 2010.
Genbank Accession No. NP_001985, Coagulation factor XIII B chain precursor, Sep. 20, 2010.
Lankhof et al., von Willebrand factor without the A2 domain is resistant to proteolysis. *Thromb. Haemost.* 77(5):1008-13 (1997).
Lowe, Factor IX and thrombosis. *Br. J. Haematol.* 115(3): 507-13 (2001).
Pietu et al., Production in *Escherichia coli* of a biologically active subfragment of von Willebrand factor corresponding to the platelet glycoprotein Ib, collagen and heparin binding domains. *Biochem Biophys Res Commun.* 164:1339-47 (1989).

(Continued)

*Primary Examiner* — Celine Qian
(74) *Attorney, Agent, or Firm* — Marshall, Gerstein & Borun LLP

(57) ABSTRACT

The present invention relates to a method to enhance cell growth in culture comprising adding an alkyl-amine-n-oxide (AANOx), such as dodecyldimethylamine oxide (DDAO), into the culture medium in an amount sufficient to improve cell growth.

18 Claims, 4 Drawing Sheets

(56) References Cited

OTHER PUBLICATIONS

Wood et al, Expression of active human factor VIII from recombinant DNA clones. *Nature*, 312(5992): 330-7 (1984).

Brycki et al., Catabolic activity of *Bacillus* genus bacteria in DDAO-containing media. *Polish J. Environ. Studies*, 4(4): 411-5 (2005).

Cserhati et al., Alkyl ehtoxylated and alkylphenol ethoxylated nonionic surfactants: Interaction with bioactive compounds and biological effects. *Environ. Health Perspect. APR*, 103(4): 358-64 (1995).

Dypbukt et al., Different prooxidant levels stimulate growth, trigger apoptosis, or produced necrosis of insulin-secreting RINm5F cells: The role of intracellular polyamines. *J. Biol. Chem.* 239(48): 30553-60 (1994).

Kozirog et al., Influence of N,N-bis(3-aminopropyl)dodecylamine on the mycelium growth and the cell wall composition of resistance and sensitive strains belonging to the genus *Aspergillus*. *Polish J. Microbiol.* 54(4): 271-8 (2005).

International Search Report and Written Opinion of the International Searching Authority, PCT/US2009/069854, dated Mar. 8, 2010.

Ryjkina et al., Molecular dynamic computer simulations of phase behavior of non-ionic surfactants. *Angew. Chem. Int. Ed. Engl.* 41(6): 983-6 (2002).

METHOD OF ENHANCING CELL GROWTH USING ALKYL-AMINE-N-OXIDE (AANOX)

This application claims the priority benefit of U.S. Provisional Patent Application No. 61/141,555, filed Dec. 30, 2008, herein incorporated by reference.

FIELD OF THE INVENTION

The present invention relates, generally, to methods of enhancing cell growth in serum free medium by the addition of an alkyl-amine-n-oxide (AANOx), such as dodecyldimethylamine oxide (DDAO) to cell culture medium. The addition of DDAO to the culture medium improves cell growth rate, thereby improving production of recombinant protein expressed by the cells.

BACKGROUND OF THE INVENTION

In vitro cultivation of cells, particularly eukaryotic cells, and more specifically mammalian cells, often requires special culture media that make available the growth nutrient substances that are required for efficient growth of the cells. For the efficient production of biological products from these cultured cells, including viruses or recombinant proteins, it is important that an optimal cell density is achieved as well as an increase in protein expression to obtain maximal product yield.

Cell culture media provide the nutrients necessary to maintain and grow cells in a controlled, artificial and in vitro environment. Characteristics and composition of the cell culture media vary depending on the particular cellular requirements. Relevant culture parameters include osmolarity, pH, and nutrient formulations. Cell culture media formulations have been supplemented with a range of additives, including undefined components like fetal calf serum (FCS), several animal derived proteins and/or protein hydrolysates of bovine origin.

In general, serum or serum-derived substances, such as albumin, transferrin or insulin, may contain unwanted agents that contaminate the cell cultures and the biological products obtained therefrom. For example, human serum derived additives have to be tested for all known viruses, including hepatitis and HIV, that can be transmitted by serum. Moreover, bovine serum and products derived therefrom bear the risk of bovine spongiform encephalopathy (BSE) contamination. In addition, all serum-derived products can be contaminated by unknown constituents. In the case of serum or protein additives that are derived from human or other animal sources in cell culture, there are numerous problems (e.g., the varying quality in composition of the different batches and the risk of contamination with mycoplasma, viruses or BSE), particularly if the cells are used for production of drugs or vaccines for human administration.

Many attempts have been made to provide efficient host systems and cultivation conditions, which do not require serum or other animal protein compounds. Simple serum free medium typically includes basal medium, vitamins, amino acids organic or inorganic salts, and optionally additional components to make the medium nutritionally complex.

Soy hydrolysates are known to be useful for fermentation processes and can enhance the growth of many organisms, yeasts and fungi. WO 96/26266 describes that papaic digests of soy meal are a source of carbohydrate and nitrogen and many of the components can be used in tissue culture. Franek et al. (Biotechnology Progress 16:688-692, 2000) describe growth and productivity promoting effects of defined soy hydrolysate peptide fractions.

WO 96/15231 discloses serum-free medium composed of the synthetic minimal essential medium and yeast extract for propagation of vertebrate cells and virus production process. A medium formulation composed of a basal cell culture medium comprising a rice peptide and an extract of yeast and enzymatic digest thereof, and/or a plant lipid for growth of animal cells is disclosed in WO 98/15614. A medium comprising purified soy hydrolysate for the cultivation of recombinant cells is disclosed in WO 01/23527. WO 00/03000 discloses a medium that comprises a soy hydrolysate and a yeast extract, but also requires the presence of recombinant forms of animal proteins, such as growth factors.

EP 0481791 describes a biochemically defined culture medium for culturing engineered CHO cells, which is free from protein, lipid and carbohydrate isolated from an animal source, further comprising a recombinant insulin or insulin analogue, 1% to 0.025% w/v papain digested soy peptone and putrescine. WO 98/08934 describes a serum-free eukaryotic cell culture comprising hydrolyzed soy peptides (1-1000 mg/L), 0.01 to 1 mg/L putrescine and a variety of animal-derived components, including albumin, fetuin, various hormones and other proteins. In this context, it should be also noted that putrescine is also known to be contained in standard media like DMEM/Ham's F12 in a concentration of 0.08 mg/L.

Often cell culture media may comprise trace amounts of contaminants such as detergents or preservatives which are used to prepare the components of the media. Surfactants and detergents such as N-oxides of lipid amines, Triton-X, Nonidet P40, sodium dodecyl sulfate (SDS), CHAPS, and polysorbate, to name a few, are commonly used in biochemical processes to wash solutions, membranes, glassware and many processes relied upon in recombinant biology and in biochemistry. For example, the nonionic detergent N,N-dimethyldodecylamine-N-oxide (DDAO) $(CH_3(CH_2)_{11}N(O)(CH_3)_2)$ (CAS number: 1643-20-5) or related compounds, alkylamine-N-oxides, are used in many areas, including cosmetics, genetic engineering, and for the study of protein membranes (Brycki et al., Polish Journal of Environmental Studies 14:411-15, 2005). DDAO is also used in the manufacturing of soy hydrolysate compounds, which are common additives in serum free media. Trace amounts of DDAO could then be detected in cell culture media that have been supplemented with contaminated soy hydrolysates. It is typically held that these trace amounts of contaminants do not effect the growth or viability of cells in culture, however, Brycki et al. (supra) studied the effects of DDAO on the denitrification (conversion of $NO_3^-$ to $N_2$) of *Bacillus* bacteria in culture, and showed that DDAO levels above 75 parts per million slowed the process of denitrification. However, no analysis of the effects of these trace contaminants such as DDAO in mammalian cell culture has been performed to date.

Thus there remains a need to determine the effects of culture media contaminants of cell proliferation in order to increase the growth rate of cells, and to provide an optimal cell culture medium for production of biological products, such as those used as pharmaceuticals or vaccines in humans.

SUMMARY OF THE INVENTION

The present invention is directed to improvement of cell culture conditions by addition of an alkyl-amine-n-oxide (AANOx) to cell culture media.

In one aspect, the invention provides a method for enhancing expression of recombinant protein in cell culture comprising culturing cells that express the recombinant protein in culture media comprising an amount of alkyl-amine-n-oxide (AANOx) sufficient to improve the growth rate of the cells in culture.

In a related aspect, the invention contemplates a method for enhancing growth rate of cells in cell culture comprising culturing cells in culture media comprising an amount of alkyl-amine-n-oxide (AANOx) sufficient to improve the growth rate of the cells in culture.

In one embodiment the AANOx is selected from the group consisting of dimethyl-tetradecyl-amine-oxide ($C_{14}NC_2O$), dimethyl-hexadecyl-amine-oxide ($C_{16}NC_2O$), and analytes of alkyl-amine-n-oxide, wherein the alkyl includes, C10, C12, C14, and C16, (e.g., $C_{12}NC$, $C_{12}NC_2$, $C_{14}NC$, $C_{14}NC_2$), with or without additional methyl branches. In a related embodiment, the AANOx is dodecyldimethylamine oxide (DDAO).

In one embodiment, the amount of AANOx is between about 4 and about 80 parts per billion (ppb) (corresponding to about 1 to about 20 parts per million equivalent AANOx found in soy peptone preparations). In a related embodiment, the amount of AANOx is between about 4 and about 50 ppb. In another embodiment, the amount of AANOx is between about 10 ppb and about 40 ppb. It is contemplated that the AANOx is about 4, about 5, about 6, about 7, about 8, about 9, about 10, about 11 about 12, about 13, about 14, about 15, about 16, about 17, about 18, about 19, about 20, about 25, about 30, about 35, about 40, about 45, about 50, about 55, about 60, about 65, about 70, about 75 or about 80 ppb.

In some embodiments, the AANOx is added to the culture media over regular time periods to sustain the level of AANOx in the cell media. In additional embodiments, the AANOx is added over multiple time periods to sustain the level of AANOx in the cell media. In one embodiment, the AANOx is added continuously over a single time period to sustain the level of AANOx in the cell media.

In one embodiment, the AANOx is not derived from a soy hydrolysate preparation. In a related embodiment, the AANOx is derived from a soy hydrolysate preparation.

Exemplary soy hydrolysates include, but are not limited to, highly purified soy hydrolysate, purified soy hydrolysate, crude soy hydrolysate, plant-based hydrolysate, non-plant-based hydrolysate, yeast based soy hydrolystate, HYPEP 1510®, HY-SOY®, HY-YEAST 412®, HI-YEAST444®, Tryprone, casein hydrolysate, yeast extract, papain digested soy peptone, TC Yeastolate, Yeastolate UF, Soy Hydrolysate UF and HYQ® Soy Hydrolysate.

In one embodiment, the invention provides that the culture media is animal protein-free media. In another embodiment, the culture media comprises animal protein.

The invention provides that the recombinant protein is grown in cells, wherein the cells are mammalian cells. In one embodiment, the cells are selected from the group consisting of BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, CHO cells, NS-1 cells, MRC-5 cells, WI-38 cells, BHK cells, 293 cells, RK cells, chicken embryo cells and other mammalian cells useful for recombinant protein production known in the art. In a related embodiment, the cells are CHO cells.

It is contemplated that the method of the invention is useful to produce any recombinant protein. In one embodiment, the recombinant protein is a blood clotting factor. In another embodiment, the blood clotting factor is selected from the group consisting of Factor II, Factor V, Factor VII, Factor VIII, Factor IX, Factor X, Factor XI, von Willebrand Factor, Factor XII and Factor XIII. In a further embodiment, the blood clotting factor is Factor VIII.

In another aspect, the invention provides a cell culture media comprising alkyl-amine-n-oxide (AANOx) in an amount sufficient to enhance cell growth when used in the culture media.

In one embodiment the AANOx is selected from the group consisting of dimethyl-tetradecyl-amine-oxide ($C_{14}NC_2O$), dimethyl-hexadecyl-amine-oxide ($C_{16}NC_2O$), and analytes of alkyl-amine-n-oxide, wherein the alkyl includes C10, C12, C14, and C16, (e.g., $C_{12}NC$, $C_{12}NC_2$, $C_{14}NC$, $C_{14}NC_2$), with or without additional methyl branches. In a related embodiment, the AANOx is dodecyldimethylamine oxide (DDAO).

In one embodiment, the amount of AANOx is between about 4 and about 80 parts per billion (ppb) (corresponding to about 1 to about 20 parts per million equivalent DDAO found in soy peptone preparations). In a related embodiment, the amount of AANOx is between about 4 and about 50 ppb. In another embodiment, the amount of AANOx is between about 10 ppb and about 40 ppb. It is contemplated that the AANOx is about 4, about 5, about 6, about 7, about 8, about 9, about 10, about 11 about 12, about 13, about 14, about 15, about 16, about 17, about 18, about 19, about 20, about 25, about 30, about 35, about 40, about 45, about 50, about 55, about 60, about 65, about 70, about 75 or about 80 ppb.

In one embodiment, the AANOx is not derived from a soy hydrolysate preparation. In a related embodiment, the AANOx is derived from a soy hydrolysate preparation as described herein.

BRIEF DESCRIPTION OF THE DRAWINGS

FIG. 2A shows the growth enhancing effect of AANOx. FIG. 2B shows that culture of cells in high levels of AANOx is toxic.

DETAILED DESCRIPTION

Figure 1:
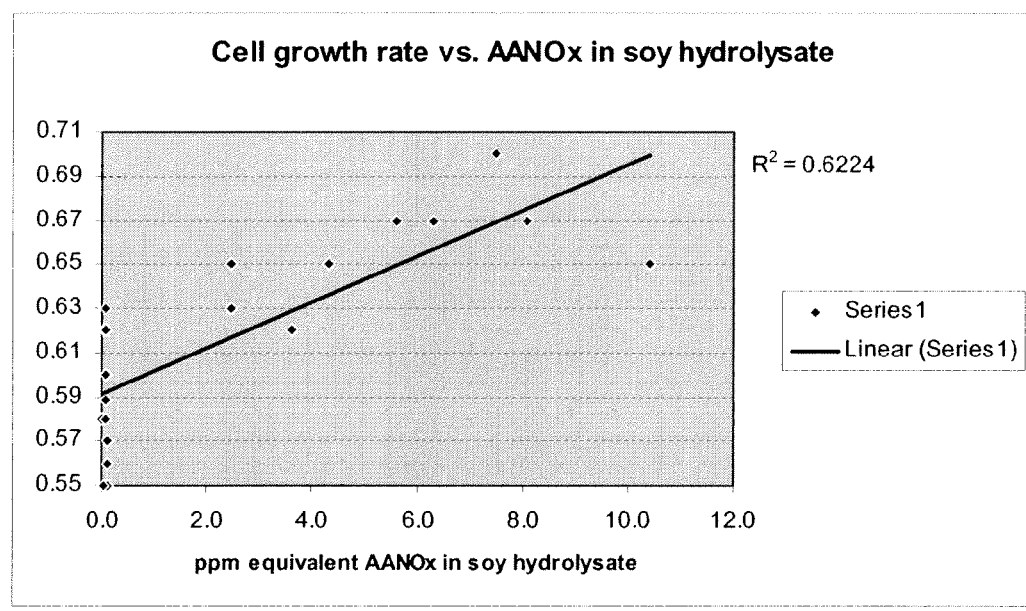
FIG. 1 shows the effect of addition of AANOx to culture cell media on CHO cell growth.

The present invention is directed to methods for enhancing cell growth in cell culture comprising adding a sufficient amount of an alkyl-amine-n-oxide (AANOx), such as dodecyldimethylamine oxide (DDAO), to enhance cell growth, and in turn, improve recombinant protein production from the cells.

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that, as used in this specification and the appended claims, the singular forms "a," "an," and "the" include plural reference unless the context clearly dictates otherwise.

As used herein, the following terms have the meanings ascribed to them unless specified otherwise.

The term "cell culture" or "culture" refers to the maintenance of cells in an artificial, in vitro environment. It is understood that the term "cell culture" is a generic term and may be used to encompass the cultivation not only of individual cells, but also of tissues, organs, organ systems or whole organisms. See U.S. Pat. No. 6,103,529.

The phrases "cell culture medium," "culture medium" (plural "media" in each case) and "medium formulation" refer to a nutritive solution for cultivating cells and may be used interchangeably.

The term "animal protein-free cell culture medium" as used herein refers to a medium that does not contain proteins and/or protein components from higher multicellular non-plant eukaryotes. Typical proteins that are avoided are those found in serum and serum-derived substances, such as and without limitation, albumin, transferrin, insulin and other growth factors. The animal protein-free cell culture medium is also free of any purified animal-derived products and recombinant animal-derived products as well as protein digests and extracts thereof or lipid extracts or purified components thereof. Animal proteins and protein components are to be distinguished from non-animal proteins, small peptides obtainable from plants (usually 10-30 amino acids in length), such as soybean, and lower eukaryotes, such as yeast which may be included into the animal protein free cell culture medium according to the invention. The term "serum-free media" is a type of "animal protein-free cell culture medium" as applied to media includes any mammalian cell culture medium that does not contain serum, such as fetal bovine serum.

The animal protein-free culture medium according to the invention is in one aspect based on any basal medium such as DMEM, Ham's F12, Medium 199, McCoy or RPMI generally known to the skilled worker. The basal medium in various embodiments comprises a number of ingredients, including by way of exemplification and without limitation, amino acids, vitamins, organic and inorganic salts, and sources of carbohydrate, each ingredient being present in an amount which supports the cultivation of a cell which is generally known to the person skilled in the art. The medium, in certain aspects, contains auxiliary substances, such as buffer substances like sodium bicarbonate, antioxidants, stabilizers to counteract mechanical stress, or protease inhibitors. If required in various embodiments, a non-ionic surfactant such as, for example and without limitation, mixtures of polyethylene glycols and polypropylene glycols (e.g. PLURONIC F68®, SERVA) are added as a defoaming agent.

The term "alkyl-amine-n-oxide" or "AANOx" refers to a family of related chemical compounds (analytes of alkyl-amine-n-oxide. In some embodiments, without limitation, the alkyl includes C10, C12, C14, and C16 carbon moieties, (e.g., $C_{12}NC$, $C_{12}NC_2$, $C_{14}NC$, $C_{14}NC_2$, etc.), with or without additional methyl branches. Additional alkyl amine oxides known and apparent to a person of skill in the art are also contemplated for use in the method of the invention.

The term "dodecyldimethylamine oxide" or "DDAO" refers to a non-ionic detergent ($C_{12}H_{25}N(CH_3)_2O$) that is used in biological applications to clear membranes and filters and various other detergent functions. In some instances, it is useful in the preparation of soy hydrolysates, which are common additives of serum free media. DDAO is often a trace contaminant in soy hydrolystate preparations. However, it has been discovered herein that small amounts of DDAO are beneficial to growth of cells in culture. In one embodiment, DDAO is added to cell culture media in order to improve growth of cells in culture. The DDAO is added in an amount sufficient to improve cell growth. It is contemplated in various aspects that DDAO is added to cell culture media in an amount between about 4 and 80 parts per billion (ppb) (i.e. between about 1 and about 20 ppm equivalent in the soy hydrolysate, for example 4 g/L soy hydrolysate having 1 ppm DDAO equals 4 ppb DDAO in cell culture). It is further contemplated that, in some embodiments, the DDAO is added to the culture media over regular time periods to sustain the level of DDAO in the cell media. In other embodiments the DDAO is added in a single bolus to the cell culture DDAO is obtained from many commercial sources. In one embodiment, the DDAO is not derived from a soy hydrolysate preparation In other embodiments, the DDAO is derived from a soy hydrolysate preparation. The description above for DDAO is applicable to any AANOx contemplated herein.

It is also contemplated that other trace detergents are useful in appropriate amounts to improve cell growth, similar to DDAO. These common cell culture media contaminants include, but are not limited to, DDAO, as well as five related DDAO analytes, including, but not limited to, dimethyl-tetradecyl-amine-oxide ($C_{14}NC_2O$) or dimethyl-hexadecyl-amine-oxide ($C_{16}NC_2O$) (similar to DDAO but with 14C or 16C chain, respectively, instead of 12C), as well as analytes that are alkyl-amine-N-oxide' (AANOx), wherein the alkyl includes, for example, C10, C12, C14, C16, (e.g., $C_{12}NC$, $C_{12}NC_2$, $C_{14}NC$, $C_{14}NC_2$), with or without additional methyl branches.

The term "hydrolysate" refers to any enzymatic digest of a vegetable or yeast extract. The "hydrolysate" in various aspects is further enzymatically digested, for example by papain, and/or formed by autolysis, thermolysis and/or plasmolysis.

Examples of non-animal based hydrolysates include, without limitation, plant-based hydrolysates and non-plant-based hydrolysates, e.g., HYPEP 1510®, HY-SOY®, HY-YEAST 412® and HI-YEAST444® (from sources such as Quest International, Norwich, N.Y., OrganoTechnie, S.A. France, Deutsche Hefewerke GmbH, Germany, or DMV Intl. Delhi, N.Y.) and yeast-based hydrolysates, e.g., Tryprone, casein hydrolysate, yeast extract, papain digested soy peptone, TC Yeastolate (BD Diagnostic) and Yeastolate UF (SAFC Biosciences). Examples of plant-based hydrolysates include Soy Hydrolysate UF (SAFC Biosciences) and HYQ®. Soy Hydrolysate (HyClone Media). See e.g., U.S. Patent Publication No. 080227136. Sources of yeast extracts and soy hydrolysates are also disclosed in WO 98/15614, WO 00/03000, WO 01/23527 and U.S. Pat. No. 5,741,705.

The plant-derived protein hydrolysate used for the animal protein-free cell culture medium according to the invention is in one aspect selected from the group consisting of a cereal hydrolysate and/or a soy hydrolysate. The soy hydrolysate in certain embodiments is a highly purified soy hydrolysate, a purified soy hydrolysate or crude soy hydrolysate.

The term "protein" as used herein refers to any protein, protein complex or polypeptide, including recombinant proteins, protein complexes and polypeptides composed of amino acid residues linked via peptide bonds. Proteins are obtained in various aspects by isolation of a protein from an in vivo source, by synthetic preparative methods or via recombinant DNA technology. Synthetic polypeptides are synthesized, for example and without limitation, using an automated polypeptide synthesizer. A recombinant protein used according to the present invention is in various aspects produced by any method known in the art as described herein below. In one embodiment, the protein is a physiologically active protein, including a therapeutic protein or a biologically active derivative thereof. The term "biologically active derivative" refers to a modified protein having substantially the same functional and/or biological properties of the parent protein. The term "protein" typically refers to large polypeptides. The term "peptide" typically refers to short polypeptides. As used herein, polypeptide, protein and peptide are used interchangeably. A "protein complex" refers to a molecule that is comprised of at least one protein bound to at least one other protein. Examples of protein complexes include, but are not limited to, a protein bound to a cofactor or chaperone protein, ligand-receptor complexes and multisubunit proteins such as integrins and other cell surface receptors comprises of multiple protein subunits.

In various embodiments, proteins contemplated for use in the methods of the invention include physiologically active proteins useful for administration to a subject. In one embodiment, the physiologically active protein is a therapeutic protein, such as a blood clotting factor. The physiologically active protein, is in another aspect, a protein or any fragment of such a protein that still retains some, substantially all, or all of the therapeutic or biological activity of the protein. In some embodiments, the protein is one that, if not expressed or produced or if substantially reduced in expression or production, would give rise to a disease. In one aspect, the protein is derived or obtained from a human.

As used herein an "analog" or "derivative" (which may be used interchangeably) refers to a polypeptide substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence. Substitutions can be conservative or non-conservative based on the physico-chemical or functional relatedness of the amino acid that is being replaced and the amino acid replacing it. Substitutions of this type are well known in the art.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

In various embodiments of the invention, when the protein is a protein analog or a fragment of the protein or analog possessing a biological activity of the protein from which the fragment or analog is derived, the protein has an amino acid sequence identical to the amino acid sequence to the corresponding portion of the human or mammalian protein. In other embodiments, the protein or fragment or analog thereof, is substantially homologous (i.e., at least 80%, 85%, 90%, 95%, 96%, 97%, 98%, or 99% identical in amino acid sequence over a length of at least 10, 25, 50, 100, 150, or 200 amino acids, or the entire length of the active agent) to a native amino acid sequence of the corresponding human or mammalian protein.

Methods for making recombinant proteins (including recombinant therapeutic proteins) and protein analogs are well-known in the art. Methods of producing cells, including mammalian cells, which express DNA or RNA encoding a recombinant protein are described in U.S. Pat. Nos. 6,048,729, 5,994,129, and 6,063,630. The teachings of each of these applications are incorporated herein by reference in their entirety.

In one embodiment, a nucleic acid construct used to express a polypeptide or fragment, or analog thereof is one which is expressed extrachromosomally (episomally) in the recombinant mammalian cell or one which integrates, either randomly or at a pre-selected targeted site through homologous recombination, into the recipient cell's genome. A construct which is expressed extrachromosomally comprises, in addition to polypeptide-encoding sequences, sequences sufficient for expression of the protein in the cells and, optionally, for replication of the construct. The construct typically includes a promoter, a polypeptide-encoding DNA sequence and a polyadenylation site. The DNA encoding the protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it includes the polypeptide-encoding nucleic acid sequences. Optionally, it includes one or more of a promoter sequence, an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

Host cells used to produce recombinant proteins are, by way of exemplification and without limitation, bacterial, yeast, insect, avian, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells include immortalized cells (a cell line) or non-immortalized (primary or secondary) cells and include any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types. In other aspects, the cells are, for example, cells producing a protein of interest without recombinant transformation, for example and without limitation, a B-cell producing an antibody, which is one aspect is transformed into an immortalized status e.g. by viral infection. The cells include for example primary cells or primary cell lines. Cells that are useful for in vitro recombinant protein production include, but are not limited to, BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, CHO cells, NS-1 cells, MRC-5 cells, WI-38 cells, BHK cells, 293 cells, RK cells, chicken embryo cells, and other mammalian, avian or insect cells known in the art useful to produce recombinant proteins.

Host cells containing the polypeptide-encoding DNA or RNA are cultured under conditions appropriate for growth of the cells and expression of the DNA or RNA. Those cells which express the polypeptide are identified using known methods, and the recombinant protein isolated and purified using known methods, either with or without amplification of polypeptide production. Identification is carried out, for example, through screening genetically modified cells displaying a phenotype indicative of the presence of DNA or RNA encoding the protein, such as and without limitation, PCR screening, screening by Southern blot analysis, or screening for the expression of the protein. Selection of cells having incorporated protein-encoding DNA is accomplished in one aspect by including a selectable marker in the DNA construct and culturing transfected or infected cells containing a selectable marker gene under conditions appropriate for survival of only those cells that express the selectable marker gene. Further amplification of the introduced DNA construct, if desired, is effected by culturing genetically modified cells under conditions appropriate for amplification for example and without limitation, culturing genetically modified cells containing an amplifiable marker gene in the presence of a concentration of a drug at which only cells containing multiple copies of the amplifiable marker gene can survive.

The cells used according to the present invention are cultivated in various aspects by a method selected from the group of batch-cultivation, feed-batch-cultivation, perfusion cultivation and chemostate-cultivation, all of which are generally known in the field.

The present invention further relates to a method for expressing a target protein such as a heterologous or autologous protein or a recombinant protein. A heterologus protein is a protein that differs from any protein normally found in the organism or host cell expressing the protein. An autologous protein is a protein that is normally found in the organism or host cell. A recombinant protein is a protein that is derived from the expression of recombinant DNA in a host cell.

Recombinant proteins which are physiologically active proteins or therapeutic proteins include, but are not limited to, cytokines, growth factors, therapeutic coagulation proteins or blood clotting factors, enzymes, chemokines, soluble cell-surface receptors, cell adhesion molecules, antibodies, hormones, cytoskeletal proteins, matrix proteins, chaperone proteins, structural proteins, metabolic proteins, and other therapeutic proteins known to those of skill in the art. Exemplary recombinant proteins which are used as therapeutics include, but are not limited to, Factor VIII, Factor VIII:C, antihemophilic factor, Factor VII, Factor IX and von Willebrand factor, erythropoietin, interferons, insulin, CTLA4-Ig, alpha-glucocerebrosidase, alpha-glucosidase, follicle stimulating hormone, anti-CD20 antibody, anti-HER2 antibody, anti-CD52 antibody, TNF receptor, and others known in the art. See, for example, Physicians Desk Reference, 62$^{nd}$ Edition, 2008, Thomson Healthcare, Montvale, N.J.

In one embodiment, the protein is a therapeutic coagulation factor or blood clotting factor, including but not limited to, Factor II, Factor V, Factor VII, Factor VIII, Factor IX, Factor X, Factor XI, von Willebrand Factor, Factor XII and Factor XIII.

In one embodiment, the protein is a recombinant von Willebrand factor (vWF) or a biologically active derivative thereof. One biologically active derivative of said pvWF is pro-vWF which contains the pro-peptide. In one example of the present invention the protein is selected from the group consisting of immature vWF including the precursor vWF molecule (pre-pro-vWF) synthesized by endothelial cells and megakaryocytes, the vWF propeptide (pro-vWF), and mature plasma-derived vWF obtained upon cleavage of the signal peptide and pro-peptide, respectively, of the precursor molecule. Further examples of biologically active derivatives of plasmatic vWF include pro-drugs which are processed or converted into the biologically active form, or are biologically active as such, truncated forms, forms having deletions, forms having substitutions, forms having additions other than pro-forms, fragments of the mature form, chimeric forms, and forms having post-translational modifications as compared to the natural form. The term "recombinant vWF (rvWF)" includes vWF obtained via recombinant DNA technology having optionally a glycosylation pattern which is pharmacologically acceptable. Specific examples thereof include vWF without A2 domain thus resistant to proteolysis (Lankhof et al., Thromb Haemost. 77:1008-1013,1997) and the vWF fragment from Val 449 to Asn 730 including the glycoprotein Ib-binding domain and binding sites for collagen and heparin (Pietu et al., Biochem Biophys Res Commun. 164:1339-1347, 1989).

vWF exists in plasma in a series of multimer forms of a molecular weight of from $1\times10^6$ to $20\times10^6$ Dalton. vWF (Genbank Accession No. NP_000543) is a glycoprotein primarily formed in the endothelial cells of mammals and subsequently secreted into circulation. In this connection, starting from a polypeptide chain having a molecular weight of approximately 220 kD, a vWF dimer having a molecular weight of 550 kD is produced in the cells by the formation of several sulfur bonds. Further polymers of the vWF with increasing molecular weights, up to 20 million Dalton, are formed by the linking of vWF dimers. It is presumed that particularly the high-molecular vWF multimers have an essential importance in blood coagulation.

vWF syndrome manifests clinically when there is either an underproduction or an overproduction of vWF. Overproduction of vWF causes increased thrombosis (formation of a clot or thrombus inside a blood vessel, obstructing the flow of blood) while reduced levels of, or lack of, high-molecular forms of vWF causes increased bleeding and an increased bleeding time due to inhibition of platelet aggregation and wound closure.

A vWF deficiency may also cause a phenotypic hemophilia A since vWF is an essential component of functional Factor VIII. In these instances, the half-life of Factor VIII is reduced to such an extent that its function in the blood coagulation cascade is impaired. Patients suffering from von Willebrand disease (vWD) or vWF syndrome frequently exhibit a Factor VIII deficiency. In these patients, the reduced Factor VIII activity is not the consequence of a defect of the X chromosomal gene, but an indirect consequence of the quantitative and qualitative change of vWF in plasma. The differentiation between hemophilia A and vWD may normally be effected by measuring the vWF antigen or by determining the ristocetin-cofactor activity. Both the vWF antigen content and the ristocetin cofactor activity are lowered in most vWD patients, whereas they are normal in hemophilia A patients. vWF products for the treatment of vWF syndrome include, but are not limited to: HUMATE-P; and, IMMUNATE®, INNO-BRAND®, and 8Y®, which therapies comprising FVIII/vWF concentrate from plasma.

In a related embodiment, the protein is Factor VIII. Factor VIII (FVIII) is a blood plasma glycoprotein of about 260 kDa molecular mass produced in the liver of mammals (Genbank Accesion No. NP_000123). It is a critical component of the cascade of coagulation reactions that lead to blood clotting. Within this cascade is a step in which Factor IXa, in conjunction with FVIII, converts Factor X (Genbank Accession No. NP_000495) to an activated form, Factor Xa. FVIII acts as a cofactor at this step, being required with calcium ions and phospholipid for the activity of Factor IXa. The two most common hemophilic disorders are caused by a deficiency of functional FVIII (Hemophilia A, about 80% of all cases) or functional Factor IXa (Hemophilia B or Christmas Factor disease). FVIII circulates, in plasma at a very low concentration and is bound non-covalently to vWF. During hemostasis, FVIII is separated from vWF and acts as a cofactor for activated Factor IX (FIXa)-mediated Factor X (FX) activation by enhancing the rate of activation in the presence of calcium and phospholipids or cellular membranes.

FVIII is synthesized as a single-chain precursor of approximately 270-330 kD with the domain structure A1-A2-B-A3-C1-C2. When purified from plasma, FVIII is composed of a heavy chain (A1-A2-B) and a light chain (A3-C1-C2). The molecular mass of the light chain is 80 kD whereas, due to proteolysis within the B domain, the heavy chain is in the range of 90-220 kD.

FVIII is also synthesized as a recombinant protein for therapeutic use in bleeding disorders. Various in vitro assays have been devised to determine the potential efficacy of recombinant FVIII (rFVIII) as a therapeutic medicine. These assays mimic the in vivo effects of endogenous FVIII. In vitro thrombin treatment of FVIII results in a rapid increase and subsequent decrease in its procoagulant activity, as measured by in vitro assay. This activation and inactivation coincides with specific limited proteolysis both in the heavy and the light chains, which alter the availability of different binding epitopes in FVIII, e.g., allowing FVIII to dissociate from vWF and bind to a phospholipid surface or altering the binding ability to certain monoclonal antibodies.

An important advance in the treatment of hemophilia A was the isolation of cDNA clones encoding the complete 2,351 amino acid sequence of human FVIII (see, Wood et al, Nature, 312: 330 (1984) and U.S. Pat. No. 4,757,006) and the provision of the human FVIII gene DNA sequence and recombinant methods for its production. FVIII products for the treatment of hemophilia include, but are not limited to: ADVATE® (Antihemophilic Factor (Recombinant), Plasma/Albumin-Free Method, rAHF-PFM), recombinant Antihemophilic Factor (BIOCLATE™, GENARC®, HELIXATE FS®, KOATE®, KOGENATE FS®, RECOMBINATE®); MONOCLATE-P®, purified preparation of FVIII:C, Antihemophilic Factor/vWF Complex (Human) HUMATE-P® and ALPHANATE®, Anti-hemophilic Factor/vWF Complex (Human); and HYATE C®, purified pig FVIII. ADVATE®, is produced in CHO-cells and manufactured by Baxter Healthcare Corporation. No human or animal plasma proteins or albumin are added in the cell culture process, purification, or final formulation of ADVATE®.

Factor VII (also know in the art as proconvertin), a serine protease enzyme, is one of the central proteins in the blood coagulation cascade (Genbank Accession No. NP_000122). The main role of Factor VII (FVII) is to initiate the process of coagulation in conjunction with tissue factor (TF). Upon vessel injury, TF is exposed to the blood and circulating Factor VII. Once bound to TF, FVII is activated to FVIIa by different proteases, among which are thrombin (Factor IIa), activated Factor X and the FVIIa-TF complex itself. Recombinant human Factor VIIa (NOVOSEVEN®) has been introduced for use in uncontrollable bleeding in hemophilia patients who have developed inhibitors against replacement coagulation factor.

Factor IX (FIX, or Christmas Factor) (Genbank Accession No. NP_000124) is a serine protease that is inactive unless activated by Factor XIa or Factor VIIa (of the tissue factor pathway). When activated into Factor IXa, it acts by hydrolyzing an arginine-isoleucine bond in Factor X to form Factor Xa. Factor VIII is a required cofactor for FIX protease activity (Lowe G D, Br. J. Haematol. 115: 507-13, 2002). Deficiency of Factor IX causes hemophilia B or Christmas disease.

Additional blood factors amendable to use in methods of the invention include without limitation Factor II (as know in the art as thrombin) (Genbank Accession No. NP_000497), deficiencies of which cause thrombosis and dysprothrombinemia; Factor V, (Genbank Accession No. NP_000121), deficiencies of which cause hemorrhagic diathesis or a form of thrombophilia, which is known as activated protein C resistance, Factor XI (Genbank Accession No. NP_000119), deficiencies of which cause Rosenthal's syndrome (hemophilia C), and Factor XIII subunit A (Genbank Accession No. NP_000120) and subunit B (Genbank Accession No. NP_001985), deficiencies of which are characterized as a type I deficiency (deficiency in both the A and B subunits) and type II deficiency (deficiency in the A subunit alone), either of which can result in a lifelong bleeding tendency, defective wound healing, and habitual abortion; Factor XII (Genbank Accession No. NP_000496); protein C (Genbank Accession No. NP_000303); antithrombin III (Genbank Accession No. NP_000479), and activated forms thereof.

Kits are also contemplated within the scope of the invention. A typical kit comprises in various aspects an amount of AANOx, such as DDAO, in sufficient quantities such that when added to cell culture media the AANOx enhances growth of the cells in vitro. It is contemplated that the AANOx composition in the kit is prepared in, for example and without limitation, a unit dosage form, such as in a vial or dropper bottle. The kit optionally includes reagents and buffers for preparation of the samples.

Additional aspects and details of the invention will be apparent from the following examples, which are intended to be illustrative rather than limiting.

EXAMPLES

Example 1

Culture with AANOx Improves Cell Growth

Cell culture of cells recombinantly producing protein for administration of recombinant proteins to human sis often carried out in serum free media to avoid possible contamination with animal protein. However, optimal cell culture requires supplemental protein in the media. This need for non animal protein has been supplemented by use of soy hydrolysates in cell culture media. However, growth and viability issues have been experienced by some manufacturers using soy hydrolysate materials from commercial suppliers since early 2006. This issue is possibly related to a non-ionic surfactant present in the soy peptone preparation, such as dimethyldodecylamine oxide (DDAO). This compound present in some liquid cleaners is used to regenerate the filtration membranes in the manufacturing process of the soy hydrolysate at some suppliers. Contamination with DDAO has been identified as the source of reduced cell growth in some instances.

In order to determine the effect of DDAO levels in cell growth, experiments were undertaken using CHO cells expressing FVIII with varying levels of DDAO equivalent to the contaminating amount in certain lots of commercial soy hydrolysate. Interestingly, some cell culture batches experienced the opposite effect on their cells, i.e., increased growth rate.

Cells from a bioreactor containing CHO cells in BAV serum free media, DMEM/HAM's F12 medium (11.76 g) supplemented with soya-peptone (4 g), ethanolamine (1.53 mg), L-glutamine (0.6 g), NaHCO$_3$ (2.0 g) and SYNPERONIC (PLURONIC®) F68 (0.25 g) (see International Patent Publ. WO/2006/045438) were cultured with 4 g/L soy peptone in 60 mL Roux flasks. Roux flasks provide a static, unmoving environment for the cells to grow.

These results show that DDAO has a positive effect on cell growth up to 20 parts per million (ppm) equivalent in the soy hydrolysate, but shows toxicity above 21.5 ppm.

Experiments were then carried out using AANOx at varying concentrations in Erlen shake flasks. FIG. 1 shows that AANOx added at different concentrations, (in equivalent ppm soy peptone) improves cell growth when cultured from 1 to 10 ppm (i.e., from 4 to 40 ppb).

Figure 2:
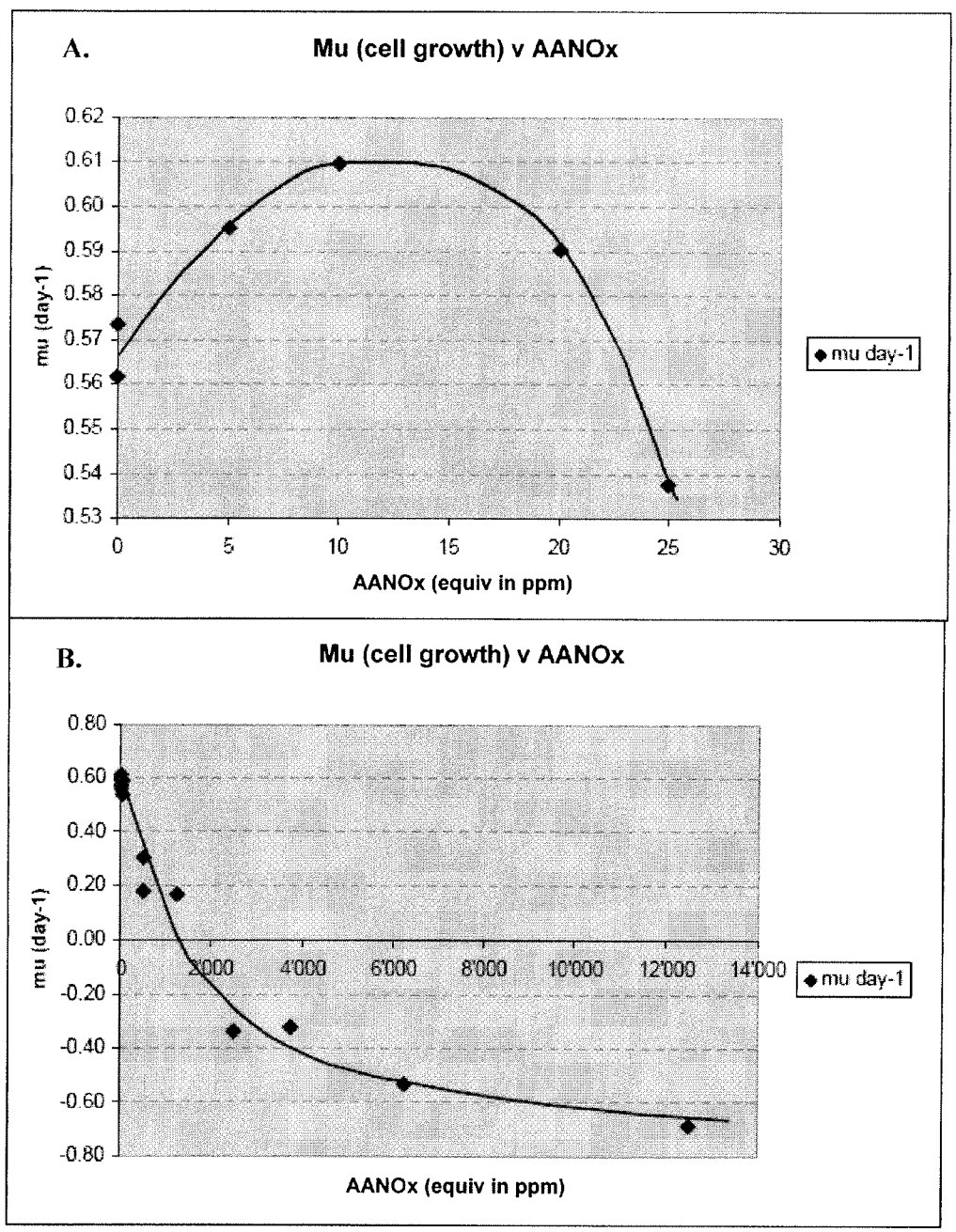
FIG. 2 shows the effects of AANOx on cell growth in media spiked with varying levels of AANOx.

A comparison of growth of groups of CHO cells all seeded in Erlen shake flasks but cultured in different media showed that AANOx (DDAO) had no toxic effect below an AANOx content in the medium of 2000 ppb, or below a AANOx equivalent content in the soy peptone of 500 ppm. Results of these experiments show that AANOx has a growth promoting effect which is dose-dependent, from 0 to 20 ppm soy peptone equivalent (0 to 80 ppb) and has a growth enhancing effect and above 20 ppm soy peptone equivalent the effect is growth limiting. AANOx also has a strong cytotoxic effect, above 1250 ppm soy peptone equivalent (FIGS. 2A and 2B).

Figure 3:
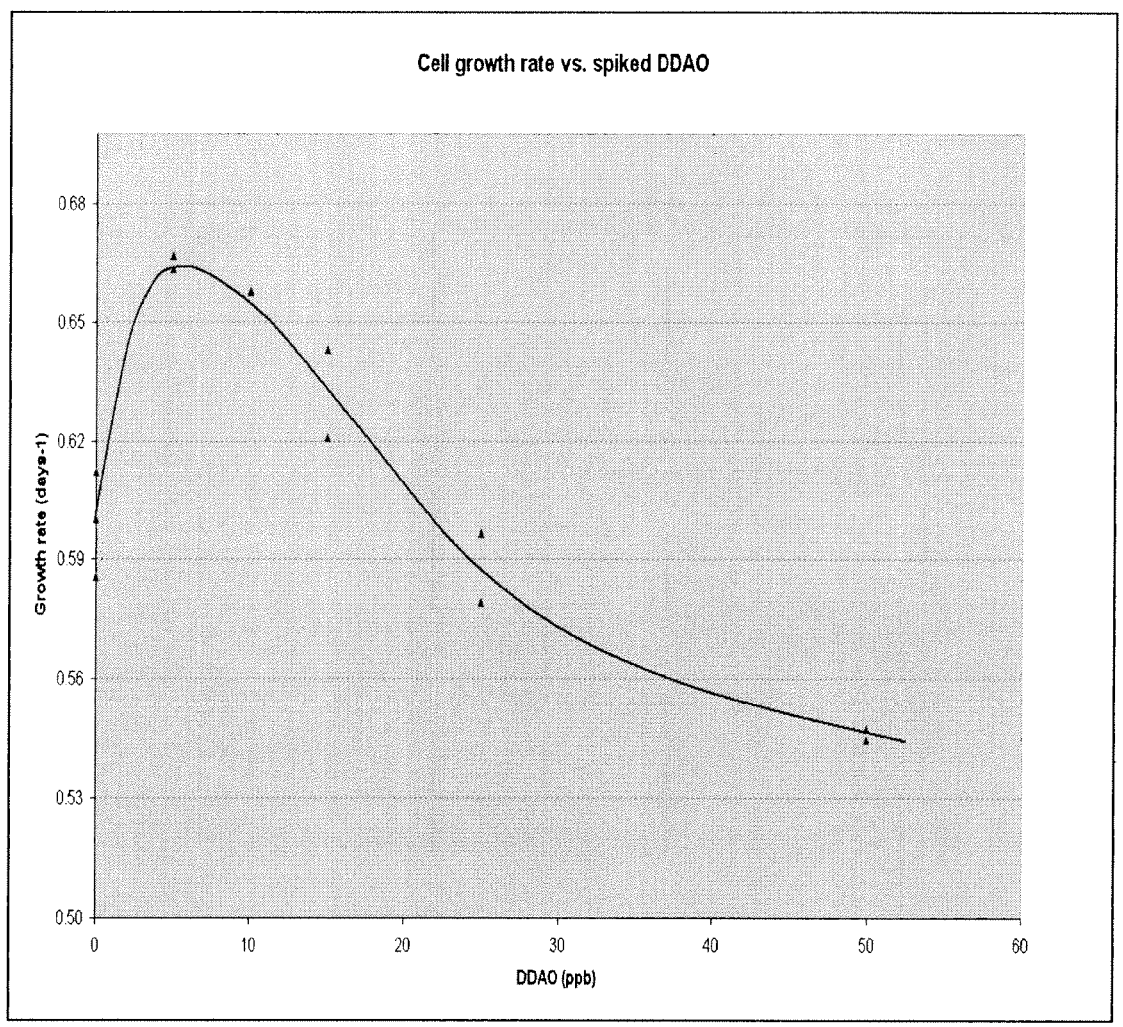
FIG. 3 illustrates the growth enhancing effect of DDAO at different cell culture concentrations, expressed in parts per billion.
Figure 4:
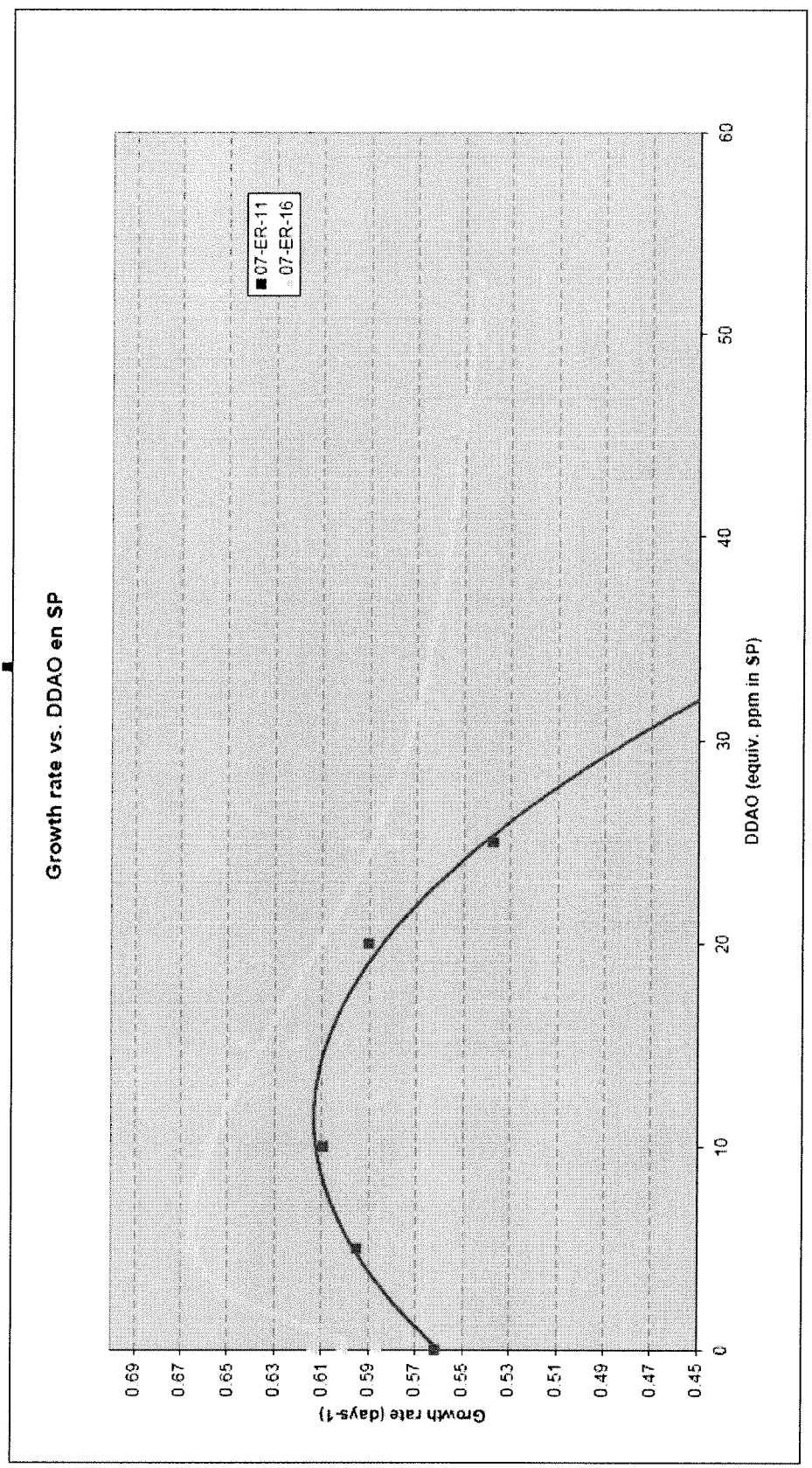
FIG. 4 illustrates the growth enhancing effect of DDAO at different cell culture conditions, and with samples assayed in duplicate. Results expressed in parts per million.

In separate experiments, DDAO was spiked into media at differing concentrations between 0-50 ppm or equivalent ppb in duplicate using serial dilution of high DDAO containing-media to reduce error (FIGS. 3 and 4). This data confirms that DDAO shows a beneficial effect on cell growth up to a certain point, in these experiments up to approximately 6-10 ppm (FIG. 4) (or 5-10 ppb, FIG. 3), and that DDAO above specific concentrations negatively effects cell growth. Additionally, there is no difference in cell viability with soy peptone at 15 ppm, formulated at 2.5 g/L or 4 g/L (consistent with spiking experiment).

Overall, the results presented herein demonstrate that DDAO supplemented into media up to a certain level, or controlled to certain levels in media already containing trace amounts of DDAO, is a beneficial way to enhance cell growth in cell culture, and in turn increase recombinant protein yield from these cells.

Numerous modifications and variations in the invention as set forth in the above illustrative examples are expected to occur to those skilled in the art. Consequently only such limitations as appear in the appended claims should be placed on the invention.

What is claimed:

1. A method for enhancing expression of recombinant protein in cell culture comprising culturing cells that express the recombinant protein in culture media comprising an amount of dodecyldimethylamine oxide (DDAO) or a related analyte sufficient to improve the growth rate of the cells in culture, wherein the analyte is selected from the group consisting of C10 dimethylamine oxide, C12 dimethyl amine oxide, C14 dimethyl amine oxide, C16 dimethylamine oxide, C18 dimethylamine oxide, dimethyl-tetradecyl-amine-oxide and dimethyl-hexadecyl-amine-oxide.

2. A method for enhancing growth rate of cells in cell culture comprising culturing cells in culture media comprising an amount of dodecyldimethylamine oxide (DDAO) or a related analyte sufficient to improve the growth rate of the cells in culture, wherein the analyte is selected from the group consisting of C10 dimethylamine oxide, C12 dimethyl amine oxide, C14 dimethyl amine oxide, C16 dimethylamine oxide, C18 dimethylamine oxide, dimethyl-tetradecyl-amine-oxide and dimethyl-hexadecyl-amine-oxide.

3. The method of claim 1 wherein the amount of DDAO or a related analyte is between about 4 and about 80 ppb.

4. The method of claim 1 wherein the amount of DDAO or a related analyte is between about 4 and about 50 ppb.

5. The method of claim 1 wherein the amount of DDAO or a related analyte is between about 10 ppb and about 40 ppb.

6. The method of claim 1 wherein DDAO or a related analyte is added over regular time periods to sustain the level of DDAO or a related analyte in the cell media.

7. The method of claim 6 wherein DDAO or a related analyte is added over multiple time periods to sustain the level of DDAO or a related analyte in the cell media.

8. The method of claim 6 wherein DDAO or a related analyte is added continuously over a single time period to sustain the level of DDAO or a related analyte in the cell media.

9. The method of claim 1 wherein the DDAO or a related analyte is not derived from a soy hydrolysate preparation.

10. The method of claim 1 wherein the DDAO or a related analyte is derived from a soy hydrolysate preparation.

11. The method of claim 1 wherein the culture media is animal protein-free media.

12. The method of claim 1 wherein the culture media comprises animal protein.

13. The method of claim 1 wherein the cells are mammalian cells.

14. The method of claim 13 where the cells are selected from the group consisting of BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, CHO cells, NS-1 cells, MRC-5 cells, WI-38 cells, BHK cells, 293 cells, and RK cells.

15. The method of claim 13 wherein the cells are CHO cells.

16. The method of claim 1 wherein the recombinant protein is a blood clotting factor.

17. The method of claim 16 where in the blood clotting factor is selected from the group consisting of Factor II, Factor V, Factor VII, Factor VIII, Factor IX, Factor X, Factor XI, von Willebrand Factor, Factor XII and Factor XIII.

18. The method of claim 17 wherein the blood clotting factor is Factor VIII.

* * * * *